United States Patent [19]
Nolan

[11] 3,952,727
[45] Apr. 27, 1976

[54] VENT DEVICE FOR OSTOMY APPLIANCE

[75] Inventor: John L. Nolan, Glenview, Ill.

[73] Assignee: Hollister Incorporated, Chicago, Ill.

[22] Filed: Dec. 5, 1974

[21] Appl. No.: 529,961

Related U.S. Application Data

[63] Continuation of Ser. No. 401,337, Sept. 27, 1973, abandoned.

[52] U.S. Cl. ............................ 128/283; 55/387; 128/1 R
[51] Int. Cl. ........................................... A61f 5/44
[58] Field of Search ............... 128/1 R, 275, 6, 283, 128/295, 294; 55/387, 389, 364

[56] References Cited
UNITED STATES PATENTS

| | | | |
|---|---|---|---|
| 2,555,086 | 5/1951 | Guinn | 128/283 |
| 2,679,248 | 5/1954 | Fullaway | 128/283 |
| 3,575,170 | 4/1971 | Clark | 128/275 |
| 3,759,260 | 9/1973 | Nolan et al. | 128/283 |

*Primary Examiner*—Lawrence Charles
*Attorney, Agent, or Firm*—Wegner, Stellman, McCord, Wiles & Wood

[57] ABSTRACT

A vent device for use with an ostomy appliance of the type utilized for venting gas from an abdominal opening following surgery comprising a filter disc of matted fibers and charcoal particles covered by an inner pervious film and an outer impervious film with an aperture for exhausting gas, together with an annular adhesive member having an adhesive surface including an inner peripheral portion adhesively secured to an outer peripheral portion of the outer impervious film and an outer peripheral portion adhesively attachable to an ostomy appliance around a vent opening therein.

2 Claims, 4 Drawing Figures

U.S. Patent  April 27, 1976  3,952,727
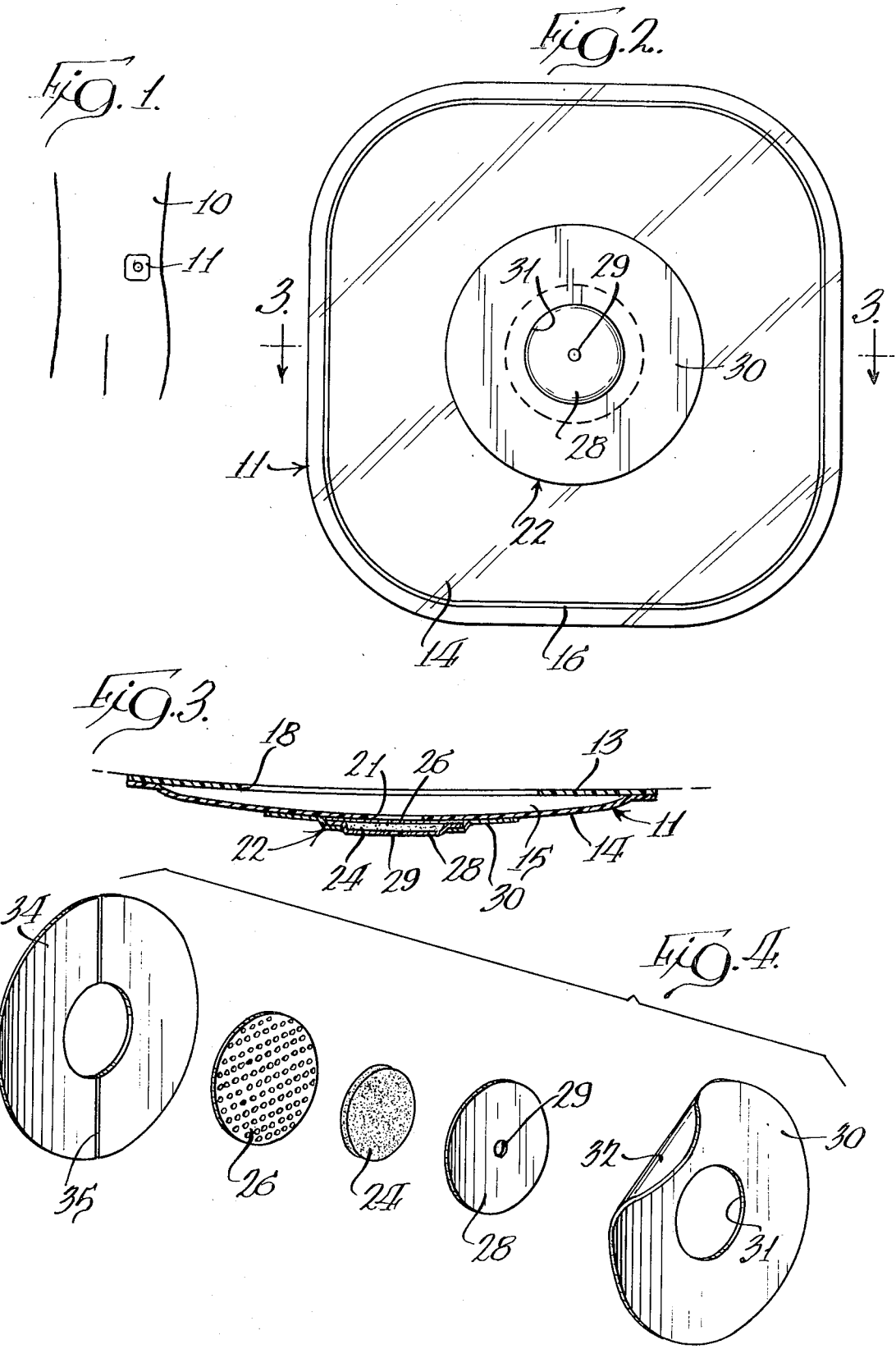

VENT DEVICE FOR OSTOMY APPLIANCE

CROSS-REFERENCE

This application is a continuation of my copending application Ser. No. 401,337, filed Sept. 27, 1973, and assigned to the same assignee as the instant application now abandoned.

BACKGROUND OF THE INVENTION

This invention relates to a vent device for an ostomy appliance in the form of a pouch with a vent for exhausting gas from an abdominal opening following surgery. Certain abdominal surgery procedures, such as a colostomy, a cecostomy and an ileostomy, result in an opening in the abdominal wall, sometimes referred to as a stoma, which permits drainage from the intestinal tract. Following such surgery, the patient is sometimes unable to control the drainage of liquids and solids and the exhaust of gas, as a result of which various drainage and collection appliances have been utilized.

For example, it has been conventional to utilize a drainage collection pouch together with means for sealing the pouch to the abdomen around the abdominal opening, so that the pouch is constantly in position to collect liquid and solid drainage at all times. The prior application of Nolan et al for U.S. Letters Patent Ser. No. 181,961, filed Sept. 20, 1971 (now U.S. Pat. No. 3,759,260), and assigned to the assignee of this application, relates to drainage collection pouches provided with vent means for exhausting gases. Also, the prior application of Nolan et al for U.S. Letters Patent Ser. No. 290,149, filed Sept. 18, 1972 (now U.S. Pat. No. 3,804,091), relates to a drainage collection pouch with vent means and an absorbent pad for absorbing wet drainage.

Some collection pouches are utilized in circumstances which contemplate collection of substantial quantities of liquids or solids, while other pouches are utilized under circumstances which contemplate collection of little or no drainage of liquids or solids. However regardless of the collection of liquids or solids, there may be gaseous discharge. Since some of the gas may have objectionable odor, it is important that the gaseous discharge be controlled. Usually, it is not practical to collect gas in an air-tight pouch, because the gas tends to inflate the pouch, as a result of which there may be an undesirable bulge or the buildup of pressure may loosen the appliance and force it away from the patient's abdomen. Accordingly, it is desirable to provide means for venting a collection pouch utilized for controlling gaseous discharge. In view of objectionable odors, it is desirable to control the venting.

The prior applications for U.S. Letters Patent mentioned above relate to pouches in which a vent device with a charcoal filter is incorporated in the pouch construction as originally manufactured. However, in spite of the availability of pouches with vent devices constructed therein, there are many commercially available collection pouches without vent devices which are customarily utilized by many patients. It would be desirable to provide a separate attachable vent device for use in connection with collection pouches which are not originally constructed with vent devices.

SUMMARY OF THE INVENTION

The present invention relates to an attachable vent device with a filter for use with a collection pouch in association with an abdominal opening for controlling exhaust of gases from the collection pouch without objectionable odors.

A vent device embodying the principles of the present invention includes a fibrous disc with carbon particles therein, an inner cover disc on one surface of the fibrous disc having at least one aperture positionable over a vent opening in an ostomy appliance for admitting gas to the disc, an outer cover disc on the opposite surface of the fibrous disc having an aperture for exhausting gas from the fibrous disc, means securing the inner and outer cover discs together with the fibrous disc therebetween, and an adhesive disc having an aperture in register with the aperture in the outer cover disc and an adhesive surface secured to the outer cover disc and adhesively attachable to an ostomy appliance around the vent opening therein.

In a preferred embodiment of the invention, a vent device includes a filter disc of matted fibers and charcoal particles, an inner pervious film cover larger than the filter disc, an outer impervious plastic cover larger than the filter disc and the covers have outer peripheries secured together. Preferably, an adhesive protective layer is removably attached to the adhesive surface of the adhesive disc until such time as the vent device is put into use.

BRIEF DESCRIPTION OF THE DRAWINGS

FIG. 1 is a fragmentary view of the abdominal portion of a human torso, showing an ostomy appliance embodying the present invention positioned in place for use;

FIG. 2 is an enlarged outside elevational view of the ostomy appliance shown in FIG. 1, including a vent device embodying the principles of the present invention;

FIG. 3 is a transverse sectional view of the appliance shown in FIG. 2, taken at about the line 3—3 of FIG. 2;

FIG. 4 is an exploded perspective view showing the components of a vent device embodying the principles of the present invention.

DETAILED DESCRIPTION OF THE INVENTION

Referring now to the drawings in more detail, FIG. 1 illustrates a portion of a human torso 10 with an ostomy appliance 11 applied thereto. As illustrated, the appliance is in the form of a pouch, and provision is made for supporting and sealing the pouch on the abdomen to prevent leakage of fluid and uncontrolled discharge of gas.

The pouch 11 comprises a pair of generally square panels of generally similar configuration at the outer perimeter, including a substantially flat inner panel 13 adapted to be disposed adjacent the patient's body, and an outer panel 14 having a dish-shaped cross section, as seen best in FIG. 3, for purposes of providing an interior chamber 15 having some depth in a front-to-rear direction. The panels 13 and 14 are of relatively lightweight flexible plastic material which is impervious to liquid and gas and which is often transparent. The outer perimeters of the overlying panels are secured together as by heat-sealing indicated at 16 in order to form a fluid-tight pouch which is generally flat but capable of some distension.

The panel 13 includes a generally circular opening 18 adapted to be placed in register with an abdominal opening for admitting gas or drainage to the pouch. In order to seal the pouch to the abdomen to prevent leakage and support the pouch, the panel 13 preferably has a suitable adhesive coating on the exposed surface around the opening 18 adapted to removably adhere the pouch to the abdomen. While the panels 13 and 14 are illustrated as generally square in configuration, it should be understood that a vent device embodying the principles of the present invention may be utilized in connection with pouches of other construction and configuration.

In order to provide for exhaust of gas from the interior of the pouch 11, the outer panel wall 14 may be perforated by the patient to provide at least one vent aperture, as illustrated at 21 for example, to be utilized in association with a vent device 22 embodying the principles of the present invention attachable to the outer surface of the panel 14. The vent device 22 includes a circular filter disc 24 comprised of matted fibers and granular activated carbon in a commercially available form. The activated carbon functions to deodorize the gases passing from the interior of the pouch through the vent aperture 21. The surface of the disc 24 disposed toward the interior of the pouch is covered by a pervious plastic film disc 26 which is larger than the filter disc 24 and which may be made of commercially available plastic material, such as TYVEK, a product of E. I. du Pont de Nemours and Company. The opposite surface of the filter disc 24 is covered by an impervious plastic film as at 28 which is also larger than the filter disc 24 and which may be made of polyethylene, for example. The outer peripheries of the cover discs 26 and 28 are secured together as by heat-sealing in a manner to capture the filter disc 24 between central portions of the two discs 26 and 28. One or both of the cover sheets 26 and 28 may become somewhat cup-shaped during assembly in order to appropriately embrace the filter disc 24.

The pervious cover 26 includes a number of apertures which admit gas from the interior of the chamber 15 to the filter disc 24. The outer impervious cover 28 includes a central aperture 29 which exhausts gas from the filter disc 24. The arrangement of many apertures in the pervious inner disc 26 which are radially outwardly disposed relative to the single central aperture in the outer cover 28 assures that most of the gas entering the filter disc 24 must migrate radially inwardly in order to be exhausted from the aperture 29 in the outer cover. The activated carbon in the filter disc 24 functions to deodorize the gas passing from the interior of the pouch 11 through the vent aperture 21.

In order to provide for attachment of the filter to the outer panel 14 of the pouch 11, an annular adhesive coated disc 30 has a central aperture 31 which is about the size of the filter disc 24. The surface of the disc 30 disposed adjacent the outer cover 28 is coated with adhesive as illustrated at 32. The disc 30 is applied to the outer cover 28 with the aperture 31 concentrically arranged relative to the aperture 29, so that an inner peripheral portion of the adhesive coated disc 30 is adhesively attached to an outer peripheral portion of the outer cover 28. An outer peripheral portion of the adhesive-coated disc 3 may then be attached to the outer wall 14 of the pouch 11. In order to provide for handling of the assembled filter and vent device until such time as it is to be put into use, the exposed outer peripheral portion of the adhesive coated surface of the disc 30 is protected by a removable protective layer 34 having an annular configuration approximately similar to that of the adhesive disc and preferably scored along a diametric line as at 35 to facilitate separation of the protective layer from the adhesive coated surface.

In use, the filter and vent device 22 is assembled by applying the cover layers 26 and 28 to opposite sides of the filter disc 24 and heat-sealing the outer peripheries of the discs 26 and 28 together, with the filter disc captured between the covers 26 and 28. The adhesive coated annular disc 30 is applied concentrically to the outer cover member 28, and an adhesive protective layer 34 is applied to the outer peripheral portion of the adhesive surface 32. The protective layer 34 normally remains in place until such time as the filter and vent device is put into use in association with an ostomy appliance such as the collection pouch 11 which is originally constructed without vent means. In order to utilize the vent device 22 with a pouch having no vent, the patient need only perforate the outer wall 14 of the collection pouch in a manner to provide one or more vent apertures in the nature of that illustrated at 21, remove the protective layer 34 from the adhesive surface 32, and apply the adhesive surface 32 to the pouch wall 14 generally concentrically relative to the vent aperture means 21. The vent device of the present invention thus provides the capacity for controlled exhaust of gas from a collection pouch not originally so equipped.

I claim:

1. A charcoal filter vent device for use with an ostomy appliance of the type used for venting gas from an abdominal opening following surgery, comprising,
   a. a filter disc of matted fibers and charcoal particles having opposite inner and outer surfaces,
   b. an inner pervious film disc larger than the filter disc disposed on the inner surface of the filter disc, and positionable over a vent opening in an ostomy appliance for admitting gas to the filter disc,
   c. an outer impervious cover disc larger than the filter disc, disposed on the outer surface of the filter disc, and having a central aperture therein for exhausting gas from the filter disc,
   d. said inner and outer discs having outer peripheries secured together, and
   e. an annular adhesive disc having an adhesive surface with an inner peripheral portion adhesively secured to an outer peripheral portion of the cover disc and an outer peripheral portion adhesively attachable to an ostomy appliance around a vent opening therein.

2. A charcoal filter vent device for use with an ostomy appliance for venting gas from an abdominal opening following surgery, comprising:
   a. a filter pad of matted fibers and charcoal particles having opposite inner and outer surfaces,
   b. an inner pervious film pad larger than the filter pad disposed on the inner surface of the filter pad and positioned to provide communication between the interior of the ostomy appliance and the filter pad,
   c. an outer impervious cover pad larger than the filter pad disposed on the outer surface of the filter pad and having a central aperture therein for exhausting gas from the filter pad,
   d. said inner and outer pads having outer peripheries secured together, and
   e. means for securing said vent device on said ostomy appliance with the inner pervious film pad open to the interior of the ostomy appliance and with said aperture in communication with the atmosphere outside of said appliance, whereby gases escaping from the abdominal opening and into the interior of said ostomy appliance may escape through the inner film pad, the filter pad, and through the aperture into the atmosphere.

* * * * *